United States Patent [19]
Riitano

[11] Patent Number: 5,642,998
[45] Date of Patent: Jul. 1, 1997

[54] ENDODONTIC INSTRUMENT FOR RAPID MECHANICAL WIDENING OF THE CANAL MOUTH AND SPECIFIC RECTIFICATION OF THE FIRST TWO THIRDS

[76] Inventor: Francesco Riitano, Via S. Giovanni Bosco, 11, Palazzo Sangiuliano - I-88068, Italy

[21] Appl. No.: 656,988

[22] Filed: Jun. 6, 1996

[30] Foreign Application Priority Data

Jun. 6, 1995 [IT] Italy .................... RM95A0377

[51] Int. Cl.⁶ .................................................. A61C 5/02
[52] U.S. Cl. ........................................ 433/224; 433/102
[58] Field of Search ................................... 433/102, 114, 433/116, 119, 147, 224, 87

[56] References Cited

U.S. PATENT DOCUMENTS

| | | | |
|---|---|---|---|
| 322,265 | 7/1885 | Donaldson | 433/102 |
| 621,873 | 3/1899 | Vajna | 433/102 |
| 1,168,052 | 1/1916 | Bolls | 433/102 X |
| 1,369,112 | 2/1921 | Jones | 433/102 |
| 4,231,738 | 11/1980 | Riitano et al. | |
| 4,353,696 | 10/1982 | Bridges | 433/119 |
| 4,364,730 | 12/1982 | Axelsson | 433/147 |
| 4,571,183 | 2/1986 | Nash | 433/116 |
| 4,836,780 | 6/1989 | Buchanan | |
| 4,889,487 | 12/1989 | Lovaas | 433/102 |
| 4,971,556 | 11/1990 | Ritano | |
| 4,992,048 | 2/1991 | Goof | 433/102 |

FOREIGN PATENT DOCUMENTS

| | | |
|---|---|---|
| 0136500 | 4/1984 | European Pat. Off. . |
| 2597327 | 10/1987 | France . |

*Primary Examiner*—Nicholas D. Lucchesi
*Attorney, Agent, or Firm*—Browdy and Neimark

[57] ABSTRACT

The present invention relates to an endodontic instrument for rapid mechanical widening of the canal mouth and rectification of the first two thirds of the dental root canals. It comprises a head (2, 3, 4) and an elongated conical body or tine (1) joined to the head (2, 3, 4) with a neck part (5). The tine (1) is disaligned with respect to the head (2, 3, 4) in that the neck part (5) has a straight portion (5a), coaxial with the head, and a portion (5b) with an axis which is oblique and coplanar in relation to the axes of the tine and head.

14 Claims, 3 Drawing Sheets

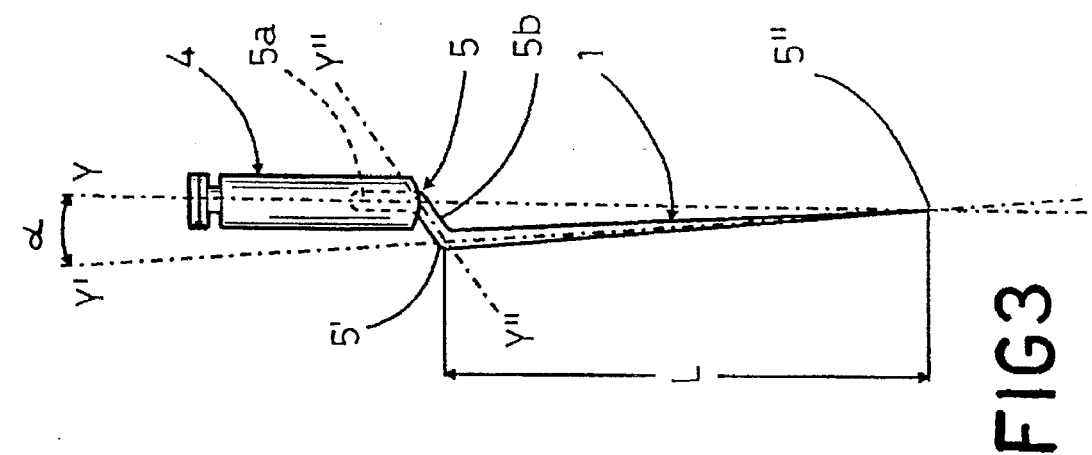
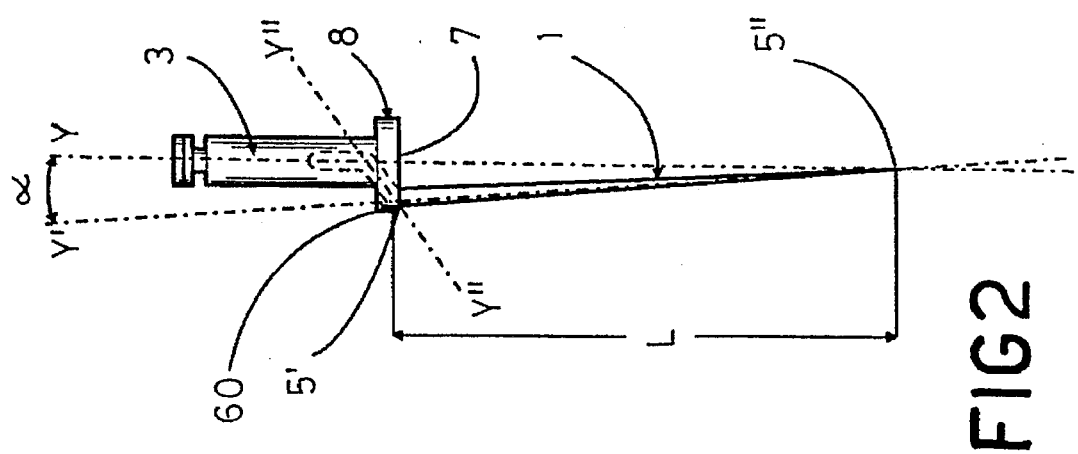
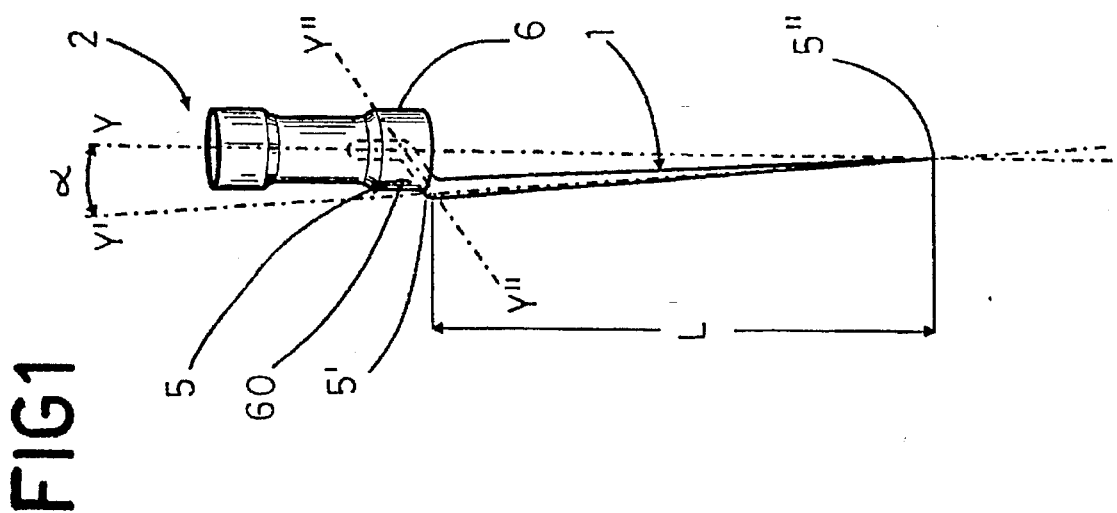

ENDODONTIC INSTRUMENT FOR RAPID MECHANICAL WIDENING OF THE CANAL MOUTH AND SPECIFIC RECTIFICATION OF THE FIRST TWO THIRDS

BACKGROUND OF THE INVENTION

The present invention relates to an endodontic instrument for rapid mechanical widening of the canal mouth and rectification of the first two thirds of the dental root canals.

It can be used in endodontic operative practice during the phase which precedes preparation of the apical third, as described in the "three-stage" technique for the preparation of the corono-apical canal devised and developed by the same Applicant.

According to this technique, preparation of the canal is performed "progressively" starting from the occlusal surface towards the apex. Ideally it divides up the tooth into three zones and three phases or "stages" associated with said zones, the methodology and the corresponding instruments.

During the first "coronal phase", the "access cavity" is formed by means of a special diamond milling kit specifically devised by the Applicant. During the second phase, the middle third is prepared and the access cavity of the middle third is aligned (rectification), this being performed using a plurality of instruments of specific shape, flexibility, diameter and length, which form the subject of a previous patent granted to the Applicant in Italy under No. 1,211,650, in Switzerland under No. 678,008, in France under No. 2,617, 704 and in the United States under U.S. Pat. No. 4,971,556. During the third phase, after completion of the preceding phases, the working length is measured at the apex and the apical third prepared.

When the second phase has been completed and prior to preparation of the apical third (third phase) of the aforementioned method, there is the need to widen further the canal mouth, eliminating completely and rapidly the remaining areas of "interference", namely those wall convexities or obstacles of a dentinal nature, which have prevented complete rectification of the first two thirds. This further widening is to be considered as particularly useful especially in the narrow and curved canals of the premolars and the upper and lower molars.

The instruments used previously during this stage include a rigid "rectifier" of the type described in Italian Patent No. 1,149,157, granted to the same Applicant. This "rectifier", indicated by 100 in FIG. 7, can be used, however, only in wide canals, such as for example those of the canines, where it works solely with the diamond-coated upper part, guided by the smooth nose 100a inserted into the middle third of the canal with an axial "in-out" and gradual lateral approach movement towards the cuspidal tip.

The most recent known instrumentation may also include titanium instruments which perform full mechanical rotation and, owing to their greater flexibility, are able to follow the curves and remain in the centre of the canals. Remaining in the centre of the canal, however, has the drawback that it widens indiscriminately "all" the wall thicknesses located around the instrument, with the risk of thinning and perforation of the thinner walls (ref. No. 50 in FIGS. 4 and 5).

The object of the present invention is therefore that of satisfying, without danger and in a locally more specific manner, the need of the endodontic procedure for widening and rectification of the first two thirds without any risk to the thinner walls in the region of the root bi- or trifurcations.

SUMMARY OF THE INVENTION

The invention, as described in the claims which follow, solves the problem of providing an endodontic instrument for rapid mechanical widening of the canal mouth and rectification of the first two thirds of the dental root canals, comprising a head (or handle) for engagement into the device for attachment to the receiving head of the contra-angle or handpiece for mechanical operation, and an elongated conical body (or tine) with a total or partial cutting or abrasive surface, joined to said head via a "neck". This body or tine, from a general point of view, is characterized in that it is disaligned with respect to the head, whereby the axis of the tine and the axis of the head define an angle α. As regards the neck, it has a straight, coaxial, internal portion fixed to said head, and a portion with an axis which is oblique and coplanar in relation to said axes.

Owing to the disalignment of the tine, rotation of the head results in the instrument describing a solid of rotation, in particular a "working cone" which may be partial or total, depending on the partial, alternating right-left rotation (FIG. 4) or total rotation (FIG. 6) imparted to the instrument.

The trajectory of the rotating tine accentuates the cutting capacity of the instrument surface, which works mainly with the upper part which describes a wider peripheral path, while the lower part has principally the function of a rotational guide pivot inside the canal.

The trajectory of movement in accordance with the solid of partial or total alternating rotation of the tine may also be associated with an axial inward or outward movement inside the canal, transmitted by the operator's hand to the instrument via the endodontic contra-angle.

The aforementioned movement, if it consists of a partial right-left alternating rotation, may be programmed so that it occurs exclusively in the direction of the "interference" or the dentinal convexity which prevents rectification of the canal passage. This may be obtained by positioning the neck of the instrument in the direction of the interference to be eliminated upon insertion of the handle into the receiving head of a contra-angle provided with a pushbutton and attachment device. If, on the other hand, the rotation is total and complete, the upper wider part of the working cone will engage, upon entry, with the diameter of the canal mouth, widening it totally. The choice between partial alternating rotation and total rotation is made by the operator, depending on type of canal, i.e. rounded or slit-shaped.

Analyzing the movement of the tine of the instrument during total rotation, said instrument having a rigidity decreasing from its neck to the tip, and comparing it with the morphology of the various canal perimeters, it was noted that the working cone has a variable position and adapts itself to the wall perimeter of the canal section, assuming a substantially vase shape according to the flexibility of the instrument and the way in which it is used (FIG. 6).

BRIEF DESCRIPTION OF THE DRAWINGS

Further characteristic features and advantages of the present invention will emerge more clearly from the detailed description which follows below, of preferred embodiments illustrated purely by way of a non-limiting example in the accompanying drawings, in which:

FIG. 1 shows a front view of a first embodiment of the instrument according to the present invention;

FIG. 2 shows a front view of a second embodiment of the instrument according to the present invention;

FIG. 3 shows a front view of a third embodiment of the instrument according to the present invention;

DESCRIPTION OF THE PREFERRED EMBODIMENTS

Figures 4, 5:
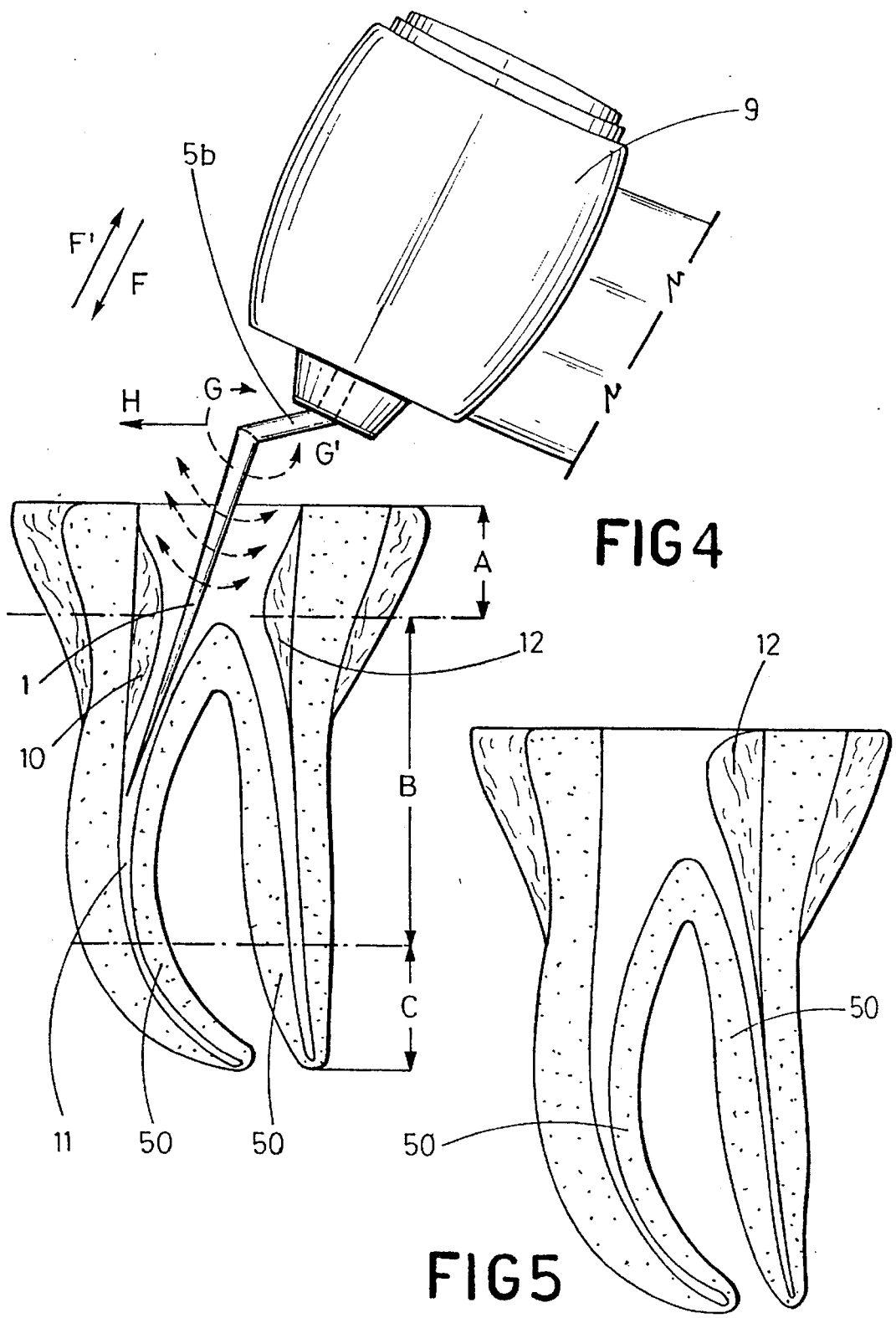
FIG. 4 shows an axonometric view of the third embodiment of the instrument fitted to a contra-angle performing a right-left alternating movement through a quarter of a turn during working of the mesial canal of a lower molar, in longitudinal section and vestibular-lingual projection.
FIG. 5 shows a cross-section of a tooth portion, one of the two canals of which has already been worked by the instrument with an alternating rotational movement, eliminating the interference 10.

FIGS. 1 to 3 show an instrument according to the invention, on a relatively true-to-life scale, with three different, conventionally known forms 2, 3, 4 of the head (or handle). In particular, the head 2, in the form of a small handgrip, is also used on particular endodontic handpieces provided with pushbuttons, while the heads 3 and 4 are respective embodiments for engagement in a receiving head of normal or special contra-angles.

The endodontic instrument for rapid mechanical widening of the canal mouth and rectification of the first two thirds of the dental root canals according to the invention is substantially a bur with an elongated conical operating body, therefore called tine below, provided with a tooth material-removing surface such as a cutting or abrasive surface, or conical tine, denoted by 1 and joined to the respective head with a neck part 5. The instrument is made of metallic material, and the cutting or abrasive surface is formed conventionally so as to remove thickness from the wall of the canal.

With reference, for the sake of greater illustrative clarity, to FIG. 3, the head, generically denoted by 2, 3, 4, has an axis Y—Y; the tine 1 has an axis Y'—Y'; the neck part 5 has a straight portion 5a, coaxial with the head, and a portion 5b with an axis Y"—Y" which is oblique and coplanar in relation to the axes Y—Y and Y'—Y' of the head and the tine.

According to the invention, therefore, the tine is disaligned with respect to the head by an angle α, which may have a different value depending on different operational requirements.

As is clearly visible in the drawing, the tip 5" of the tine 1 which is distal the head 2, 3, or 4 lies on the axis Y—Y, which is the rotation axis of the head.

In the embodiments shown in FIGS. 1 and 2, both the straight portion 5a and the oblique portion 5b of the neck are situated inside the respective heads 2 and 3.

Therefore, the heads 2 and 3 are provided with diameters such that they are able to contain the neck 5. The tine 1 projects from the head 2 and 3 in an eccentric position with respect to the head face 6 and 7, respectively, adjacent to the tine 1 and obliquely with respect thereto. The face 7 (FIG. 2) is flat and forms part of a plate 8 with diametral dimensions of about 4 mm in compliance with the standard dimensions stipulated for manual-grip handles. In this way, the head 2 may also be mounted on a handpiece without obstructing the irrigation jets emerging from the handpiece itself.

Advantageously, the heads 2 and 3 (see FIGS. 1 and 2) can be provided with a mark or sign on the handle, denoted by 60, coplanar with the plane containing the axes of the head, tine and neck, for determining the direction of the working angle of the tine.

FIG. 3 shows a third embodiment, with an instrument head 4 showing, in broken lines, the straight neck portion 5a inside the head 4, while the oblique portion 5b is situated outside of it and visible. The oblique portion 5b is generally smooth.

As regards the measurements of the instrument, with reference to FIGS. 1, 2 and 3, the conical tine has a useful working length L of between 16 and 22 mm, preferably 19 mm.

The conical tine has, in its portion bordering with said neck, a diameter 5' of between 0.35 and 1.50 mm and has, at its free end, a tip diameter 5" of between 0.08 and 0.20 mm.

The tine has a conicity ratio, and a consequent rigidity, determined by the choice of dimension for the useful working length L and the diameters 5' and 5".

FIG. 4 shows, during a working phase, the third embodiment of the instrument fitted to a contra-angle 9 and inserted into a canal 11 to be prepared. FIG. 4 shows the three parts into which, in accordance with the aforementioned "three-stage" technique of the same Applicant, the canal is divided: an upper coronal part A, following cuspidectomy, called the coronal third, a middle third B, and an apical third C. to-and-fro axial movement in the direction of the arrows F—F', together with the alternating left-and-right movement through a quarter of a turn, G—G', produces, if guided, in the direction of the arrow H, against the interference 10, 12' (shown in broken lines), or wall camber, the gradual elimination of the said interference, with widening of the mouth and consequent "rectification" of the canal passage of the first two thirds, coronal third A and middle third B.

As can be seen from FIG. 4, the instrument according to the invention has the function of further widening the canal, eliminating completely and rapidly those residual interferences which prevent the complete rectification of the first two thirds. It is possible to program in advance and in a specific manner the flaring and rectifying action against the interference during partial rotation to the right and left, as shown in FIG. 5, where the interference 10 in a mesial canal of a lower molar (FIG. 5) has been completely removed, while the interference 12 remains in the distal canal.

This "specific" elimination of the interference, as can be seen from FIG. 4, makes it possible to save considerable wall thicknesses, such as the thin distal and mesial thicknesses of the bi- and trifurcations, denoted by 50.

Figure 6:
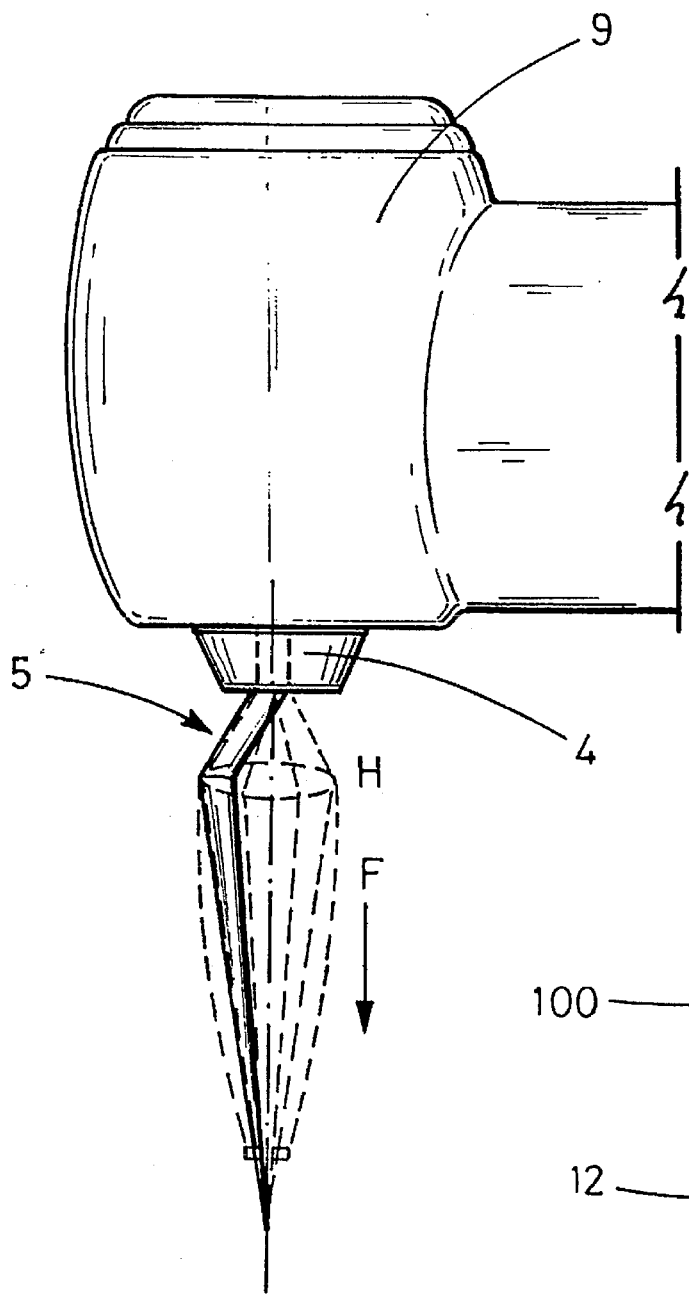
FIG. 6 shows an axonometric view of an instrument according to the present invention during continuous rotation.
Figure 7:
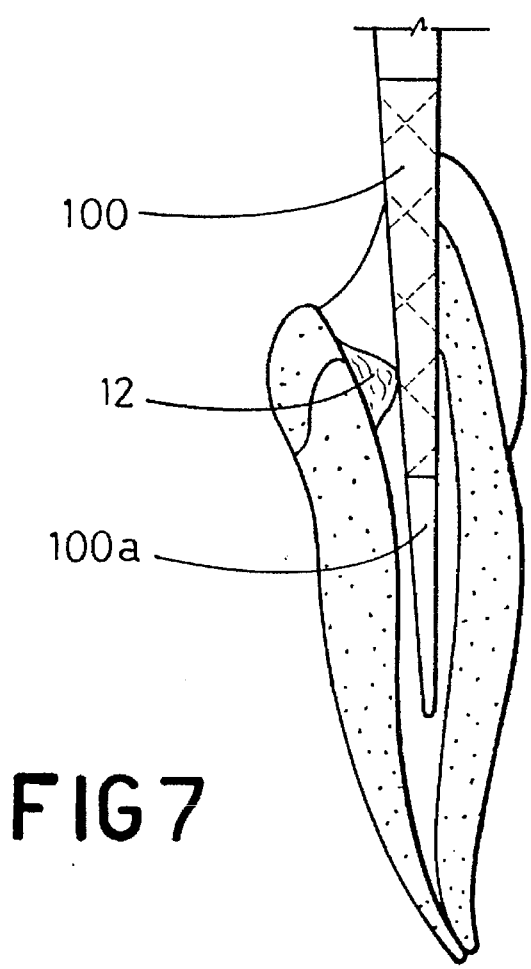
FIG. 7 shows a sagittal section through a tooth, the wide root canal of which has been worked by a rigid "rectifier" as mentioned above.

As shown in FIG. 6, the total rotational movement, in the direction of the arrow H, of the tine of the conical instrument results in a variable working cone which is adapted to the wall perimeter of the canal section, assuming a shape substantially in the form of a vase. This form may vary, as shown by the broken lines, depending on the flexibility of the instrument and the way in which it is used.

The invention thus conceived may be subject to numerous modifications and variations, all of which fall within the scope of the same innovative idea. Furthermore, all the details may be replaced by technically equivalent elements.

In practice, modifications and/or improvements are obviously possible, all of which, however, falling within the scope of the following claims.

What is claimed:

1. An endodontic instrument for rapid mechanical widening of the canal mouth and rectification of the first two thirds of dental root canals, comprising a head (2, 3, 4) for engagement in an attachment device of a contra-angle (9) or a handpiece for mechanical operation, the head defining a head axis (Y—Y), and an elongated conical tine (1) defining a tine axis (Y'—Y') and including a material-removing surface and a tip (5"), said tine being joined to said head (2, 3, 4) with a neck part (5), wherein said tine (1) is disaligned with respect to said head (2, 3, 4), such that the tine axis (Y'—Y') and the head axis (Y—Y) define an angle ($\alpha$) therebetween;

and wherein said axes (Y—Y; Y'—Y') of said head and said tine intersect at a point adjacent to said tip (5") of said tine, such that said tip is disposed generally on said head axis (Y—Y), whereby a generally conical cut is made by rotating the tine about the head axis (Y—Y).

2. The endodontic instrument as claimed in claim 1, wherein the said straight (5a) and oblique neck portions (5b) are situated inside said head (2, 3).

3. The endodontic instrument as claimed in claim 1, wherein said straight neck portion (5a) is situated inside said head (4), and said oblique neck portion (5b) is smooth and projecting from said head (4).

4. The endodontic instrument as claimed in claim 1, wherein said head (2, 3) is provided peripherally with a mark (60) indicating the plane of coplanarity of said axes (Y—Y; Y'—Y'; Y"—Y").

5. The endodontic instrument as claimed in claim 1, wherein said conical tine (1) has a useful working length (L) of between 16 and 22 mm.

6. The endodontic instrument as claimed in claim 1, wherein said conical tine (1) includes a useful working length (L) of approximately 19 mm.

7. The endodontic instrument as claimed in claim 1, wherein said conical tine (1) has, in its portion bordering with said neck, a diameter (5') of between 0.35 and 1.50 mm.

8. The endodontic instrument as claimed in claim 1, wherein said conical tine (1) has, at its free end, a tip diameter (5") of between 0.08 and 0.20 mm.

9. The endodontic instrument as claimed in claim 1, wherein said tine (1) has a conicity ratio, and a consequent rigidity, determined by the choice of dimension for a useful working length (L) and said diameters (5', 5").

10. The instrument according to claim 1, wherein the material-removing surface includes a cutting surface.

11. The instrument according to claim 1, wherein the material-removing surface includes an abrasive surface.

12. The instrument according to claim 1, wherein said neck part (5) includes a straight portion (5a) coaxial with said head, and a portion (5b) having an axis (Y"—Y") which is oblique and coplanar in relation to said head axis (Y—Y) and said tine axis (Y'—Y').

13. An endodontic system for rapid mechanical widening of the canal mouth and rectification of the first two thirds of dental root canals, comprising:

(a) an instrument comprising a head (2, 3, 4) for engagement in an attachment device of a contra-angle (9) or a handpiece for mechanical operation, the head defining a head axis (Y—Y), and an elongated conical tine (1) defining a tine axis (Y'—Y') and including a material-removing surface and a tip (5"), said tine being joined to said head (2, 3, 4) with a neck part (5), wherein said tine (1) is disaligned with respect to said head (2, 3, 4), such that the tine axis (Y'—Y') and the head axis (Y—Y) define an angle ($\alpha$) therebetween;

and wherein said axes (Y—Y; Y'—Y') of said head and said tine intersect at a point adjacent to said tip (5") of said tine, such that said tip is disposed generally on said head axis (Y—Y), whereby a generally conical cut is made by rotating the tine about the head axis (Y—Y); and (b) a rotary driver (9) including means for mounting the instrument by the head thereof and rotating the instrument about the head axis (Y—Y).

14. An endodontic method for rapid mechanical widening of the canal mouth and rectification of the first two thirds of dental root canals, comprising:

(a) providing an instrument, the instrument comprising:

a head (2, 3, 4) for engagement in an attachment device of a contra-angle (9) or a handpiece for mechanical operation, the head defining a head axis (Y—Y), and an elongated conical tine (1) defining a tine axis (Y'—Y') and including a material-removing surface and a tip (5"), said tine being joined to said head (2, 3, 4) with a neck part (5), wherein said tine (1) is disaligned with respect to said head (2, 3, 4), such that the tine axis (Y'—Y') and the head axis (Y—Y) define an angle ($\alpha$) therebetween;

and wherein said axes (Y—Y; Y'—Y') of said head and said tine intersect at a point adjacent to said tip (5") of said tine, such that said tip is disposed generally on said head axis (Y—Y);

(b) providing a rotary driver (9) including means for mounting the instrument by the head thereof and rotating the instrument about the head axis (Y—Y); and (c) rotating the instrument about the head axis (Y—Y).

* * * * *